US005985808A

United States Patent [19]

[11] Patent Number: 5,985,808
[45] Date of Patent: Nov. 16, 1999

He et al.

[54] SYNTHETIC BAR COMPOSITION COMPRISING ALKOXYLATED SURFACTANTS

[75] Inventors: Mengtao He, Wayne; Michael Fair, Hackensack, both of N.J.; Michael Massaro, Congers, N.Y.

[73] Assignee: Lever Brothers Company, New York, N.Y.

[21] Appl. No.: 08/931,111

[22] Filed: Sep. 15, 1997

Related U.S. Application Data

[63] Continuation of application No. 08/637,148, Apr. 24, 1996, abandoned.

[51] Int. Cl.[6] .................... A61K 7/50

[52] U.S. Cl. .................... 510/155; 510/152; 510/154; 510/450

[58] Field of Search .................... 510/152, 154, 510/155, 450

[56] References Cited

U.S. PATENT DOCUMENTS

| | | | |
|---|---|---|---|
| 3,312,626 | 4/1967 | Hooker | 252/152 |
| 3,312,627 | 4/1967 | Hooker | 252/152 |
| 5,154,849 | 10/1992 | Visscher et al. | 252/174.15 |
| 5,520,840 | 5/1996 | Massaro et al. | 510/152 |
| 5,540,854 | 7/1996 | Fair et al. | 510/152 |
| 5,543,072 | 8/1996 | Fost et al. | 510/151 |
| 5,683,973 | 11/1997 | Post et al. | 510/152 |
| 5,756,438 | 5/1998 | Rau et al. | 510/151 |

FOREIGN PATENT DOCUMENTS

| | | |
|---|---|---|
| 213729 | 3/1987 | European Pat. Off. . |
| 287300 | 10/1988 | European Pat. Off. . |
| 363215 | 10/1988 | European Pat. Off. . |
| 311343 | 4/1989 | European Pat. Off. . |
| 507559 | 10/1992 | European Pat. Off. . |
| 2243615 | 11/1991 | United Kingdom . |
| 2276630 | 10/1994 | United Kingdom . |
| 93/04161 | 3/1993 | WIPO . |
| 93/17088 | 9/1993 | WIPO . |

*Primary Examiner*—Necholus Ogden
*Attorney, Agent, or Firm*—Ronald A. Koatz

[57] ABSTRACT

The present invention is directed to specific synthetic bar compositions wherein relatively small amounts of specified alkoxylated nonionic surfactant has been found to enhance mildness of bar compositions without sacrificing processability and desired user properties, such as lather and bar smoothness.

14 Claims, 2 Drawing Sheets

SYNTHETIC BAR COMPOSITION COMPRISING ALKOXYLATED SURFACTANTS

This is a Continuation application of Ser. No. 08/637,148, filed Apr. 24, 1996 now abandoned.

FIELD OF THE INVENTION

The present invention relates to synthetic bar compositions (i.e., bars in which at least a significant portion of fatty acid soap has been replaced by synthetic surfactants.

BACKGROUND

Traditionally, soap has been utilized as a skin cleanser. Notwithstanding its many advantages (e.g., inexpensive, easy to manufacture into bars, having good lathering properties), soap is a very harsh chemical. Irritated and cracked skin often result from the use of soap, especially in colder climates.

In order to maintain cleaning effectiveness and reduce harshness, the art has used synthetic surfactants to replace some or all of the soap. In particular, anionic surfactants have been used because these tend to most clearly mimic the lather generation which soap readily provides. Synthetic bars and soap-based bars have significantly different processing and user properties; for example, synthetic bars often require a structurant or binder while soap-based bars do not.

Anionic surfactants, however, are still harsh. One method of reducing the harshness of anionic surfactants is to utilize other surfactants such as nonionic or other mildness surfactants (e.g., amphoteric). The use of surfactants other than anionics, however, can introduce other problems. For example, nonionic surfactants generally do not generate creamy thick lather as do anionics; and both nonionics and amphoterics, for example can be sticky and introduce processing difficulties.

For this reason, the art is always searching for materials which are milder than anionic and/or which can be used to replace at least some of the anionic surfactants, yet, which do not simultaneously seriously compromise lather generation or processing efficiency. Further, even if the anionic is not substituted, the art is always searching for materials which can substitute for inerts and/or other fillers and produce enhanced mildness.

Unexpectedly, applicants have found that these goals can be obtained by inclusion of relatively low levels of specific nonionic surfactants in specific synthetic bar compositions (i.e., structured at least partially by polyalkylene glycol). That is, at anionic to nonionic surfactant weight ratio between 1:1 to 10:1, the nonionic surfactants provide significantly enhanced mildness without sacrificing processability or lather. While not wishing to be bound by theory, it is believed that the nonionic surfactants may be interacting with anionic surfactants to form mixed-micelle type of colloidal complexes thereby reducing free anionic surfactant (known for its harshness) from the bar.

The use of alkoxylated nonionic surfactants in bar compositions per se is not new. Prior art has shown that addition of these nonionics in fatty acid soap based bars can reduce scum formation and reduce skin irritation by reducing soap residue on skin after washing in hard water. Nonionic surfactants have also been used as cosurfactants and as solvents for antibacterial agents in soap bars. They have also been used as detergents in synthetic bars in general.

World Patent No. WO 9,317,088 to Procter & Gamble, for example, teaches a soap-based bar comprising 45–90% fatty acid soap, 1–8% nonionic $C_{14-20}EO_{65-100}$ as coactive (EO: ethylene oxide), and 0.5–2% cationic polymer as mildness aid.

World Patent No. WO 9,304,161 to Procter & Gamble teaches a soap-based bar comprising 45–90% fatty acid soap, 0.5–10% $C_{14-20}EO_{20-250}$ (preferably $C_{14-20}EO_{25-80}$) as cosurfactant, and 0.5–10% acyl isethionate surfactant. The purpose of addition of small amounts of alkoxylated nonionic surfactants was to reduce the scum formation.

Patent No. GB 2,243,615 to J. Dunbar, R. Bartolo, B. Redd, and A. Keegan teaches an antibacterial toilet soap bar containing 45–94% alkali metal soap (at least 50% in Beta-phase), 2–25% solvent for antibacterial agents, 0–30% non-solvent synthetic detergents, and 0–10% fatty acid. The solvent for antibacterial agents is selected from polyethylene glycol and nonionic alkoxylated fatty alcohols in general.

Patent No. EP 311,343 to G. Dawson and G. Ridley teaches a Beta-phase toilet soap bar comprising 45–90% of soluble alkali metal soap of C8–C24 fatty acids, 0.5–45% of an alkoxylated nonionic surfactant having an HLB of 12–19.5, and 0.01 to 5% of a water-soluble polymer. The composition has improved scum control with good mildness, lathering, and transparency.

Patent No. EP 363,215 to F. Simion, R. Subramanya, R. Cantore, and D. Masucci teaches an ultra-mild skin cleansing bar comprising 25–90% (preferably 65–95%) fatty acid soap and 5–75% (preferably 5–35%) alkoxylated nonionic or anionic surfactants ($C_8E_{j>3}A$, A=OH or anionic head groups). The soap bar is claimed to be very mild and reduce skin irritation by reducing soap residue left after washing in hard water.

Patent No. EP 213,729 to A. Hight teaches a soap bar containing 5–50% fatty acid soap, 5–25% alkoxylated nonionic detergent as coactive, and 0–10% phosphate builder. High levels of soap were included in the bar composition (weight ratio of fatty acid soap to ethoxylates is 1:1 to 10:1).

Patent No. EP 287,300 to C. Adam, G. Irlam, and R. Lee teaches a soap bar made by high energy shear at low temp. (<0.40 C) comprising 20–80% fatty acid soap, 10–60% non-soap detergent that is selected from C8–C18 anionic surfactants and nonionic surfactants, such as alkoxylated alcohols in general.

Patent No. GB 2,276,630 to P. Powers teaches a laundry detergent bar contains 10–60% non-soap anionic detergent (at least 10% alkylbenzene sulphonates and alkyl sulphates), 5–60% detergent builder and 0.3–4% alkoxylated nonionic detergent. The bar gives reduced mush when left standing in water.

Patent No. EP 507,559 to S. Pratley teaches a cast-melting bar comprising 25–60% anionic, zwitterionic and nonionic (i.e. alkoxylated nonionic) surfactants in which 8–32% are fatty acid soap. Also 10–50% alcohols are included as solvents, and 1–20% of an oily skin benefit agent is included.

U.S. Pat. Nos. 3,312,626 and 3,312, 627 to D. Hooker teaches a nonionic bar composition substantially free of anionic surfactants containing 10–70% nonionic detergents, in which alkoxylated nonionic surfactants are among the candidates. The bar also contains 0–70% PEG, EO-PO and derivatives of these compounds as structurant. In order to give these bars more "soap-like" characteristics, the reference contemplates use of 10%–80% lithium soap. It is clear that use of lithium soap is unique to the invention (column 8, lines 20–23) and that use of other soaps or anionic (other than fatty acid lithium soap) is not contemplated.

The subject invention differs from the prior art referred above, alone or in combination, in that the applicants have found that relatively low levels of specific alkoxylated nonionic surfactants (i.e., having specific molecular weight, specific melting temperature, and specific hydrophilic to hydrophobic mol ratio) most effectively mitigate the skin irritation of anionic surfactants of a personal washing bar which comprise 10 to 70% of a surfactant system of which at least 50% (though no more than 40% total of total composition) is synthetic anionic surfactant.

Also novel to the art, our invention incorporated these low levels of specific alkoxylated nonionic surfactants into specific synthetic bar compositions (i.e., structured and binded at least partially by polyalkylene glycol or derivatives of polyalkylene glycol, such as EO-PO copolymer and other hydrophobically modified polyalkylene glycol) without sacrificing processability, biodegradability, and desired user properties, such as lather, bar smoothness and homogeneity.

BRIEF SUMMARY OF THE INVENTION

Applicants have now found that the use of relatively small amounts of defined alkoxylated nonionic surfactants in bar compositions comprising primarily synthetic anionic surfactant systems remarkably and unexpectedly enhances the mildness of these bars.

More specifically, applicants' invention relates to bar compositions comprising:

(a) 10% to 70% by wt. total composition of a surfactant system selected from the group consisting of anionic surfactants, nonionic surfactants (other than the specific alkoxylated nonionic surfactants defined in (c)), cationic surfactants, amphoteric surfactants and mixtures thereof;

wherein the anionic surfactant comprises at least 50%, preferably at least 60% of said surfactant system and wherein the anionic component further comprises no more than about 40% by wt. of total composition;

(b) 20% to 85% by wt., preferably 30 to 70% total composition of a bar structurant selected from the group consisting of alkylene oxide compounds having a molecular weight of from about 2000 to about 25,000, preferably 3,000 to 10,000;

$C_8$–$C_{22}$ free fatty acids, paraffin waxes; water soluble starches (e.g., maltodextrin); and $C_8$–$C_{20}$ alkanols;

wherein the alkylene oxide compounds comprise at least 20%, preferably at least 40% of said structurant system and wherein alkylene oxide compounds further comprise no more than about 70% by wt. of total composition;

It is a criticality of this invention to include the alkylene compounds in the bar composition, because the alkylene compounds serves as a dispersant and solvent for the alkoxylated nonionic surfactants of (c);

(c) 3% to 35% by wt. total composition of an alkoxylated nonionic surfactant;

wherein ratio of anionic surfactant to alkoxylated nonionic surfactant is between 1:1 to 10:1, preferably 2:1 to 7:1;

wherein ethylene oxide:hydrophobe mol ratio of said alkoxylated nonionic surfactant is between 7:1 and 40:1 (preferably between 15:1 and 25:1); This range of mol ratio is a criticality because, above this range, said alkoxylated nonionic surfactant is not as efficient at mitigating the skin irritation of anionics (see Example 1 and 2), and they are not as biodegradable. Below this range, the said alkoxylated nonionic surfactant can cause processing problems, such as stickiness during chill-rolling and plodding, and cause undesired user properties, such as mush and reduced lather;

wherein the melting temperature of the nonionic surfactant is between 25° C. and 85° C., preferably between 40° C. and 65° C.;

wherein the molecular weight of the said nonionic surfactants is between 500 and 3000 Dalton, preferably between 1000 and 2500 Dalton.

The composition may optionally comprise 0% to 25%, preferably 2% to 15% by wt. solvent such as ethylene oxide or propylene oxide.

DETAILED DESCRIPTION OF THE INVENTION

Figure 1:
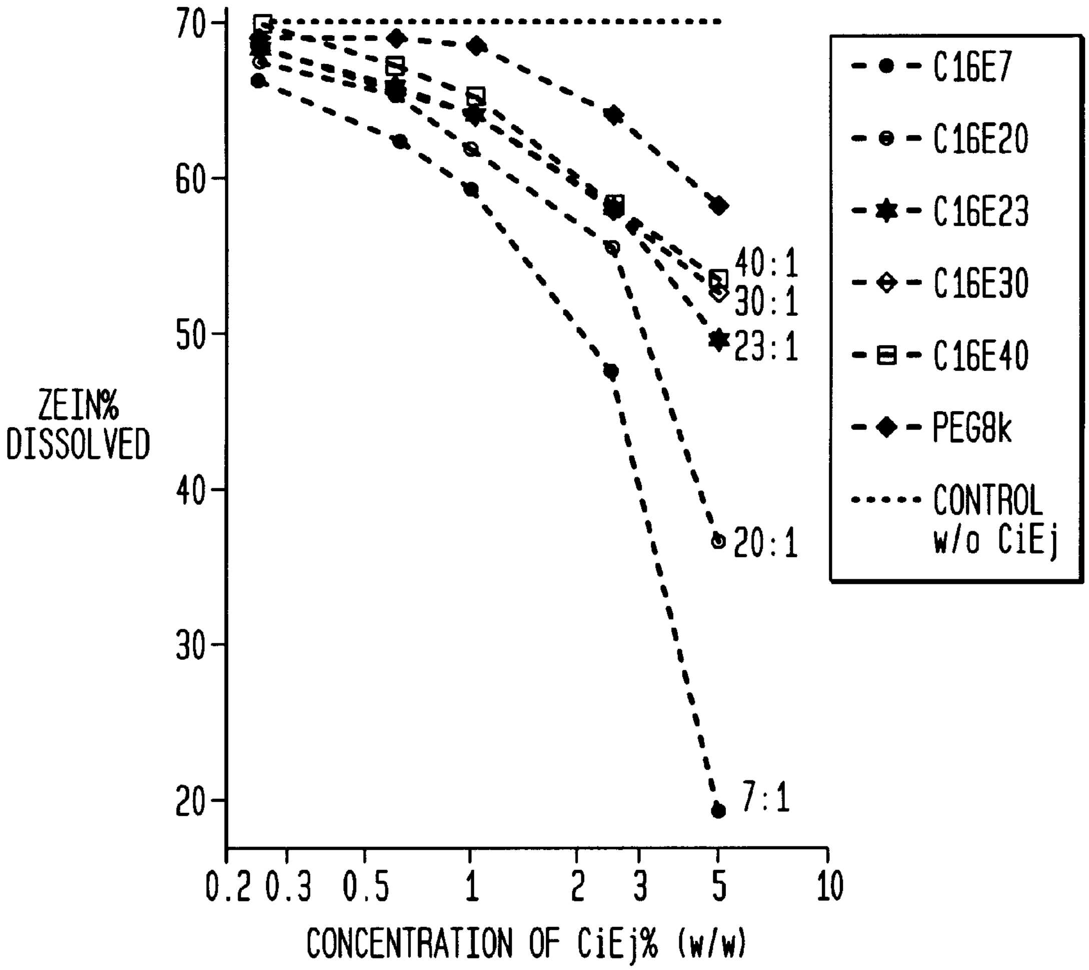
FIG. 1 shows the Zein % dissolved by acyl isethionate/cocoamidopropyl betaine as a function of alkoxylated nonionic surfactant concentration. In contrast to PEG 8000, alkoxylated nonionic surfactants significantly reduced the Zein % dissolved at even quite low levels of addition.

The present invention relates to synthetic bar compositions wherein the majority of the surfactant system of the bar comprises anionic surfactant; and to specific nonionic copolymers which can be used in such bar compositions to significantly enhance bar mildness.

More specifically, the bar compositions comprise (a) 10% to 70% by weight total composition of a surfactant system wherein said surfactant system comprises surfactants selected from the group consisting of anionic surfactants, nonionic surfactants (other than the alkoxylated nonionic surfactants of (c)), amphoteric surfactants, cationic surfactants and mixtures thereof, wherein the anionic comprises 50% or more, preferably 60% or more, of the surfactant system and the anionic further comprises no more than 40% of the total composition;

(b) Structurant System: 20% to 85%, preferably 30% to 70% by wt. total composition of a bar structurant selected from the group consisting of alkylene oxide compounds having a MW of from about 2,000 to 25,000 (which may optionally include 1% to 5% higher molecular weight polyalkylene glycols having MW from 50,000 to 500,000, especially around 100,000); $C_8$ to $C_{24}$, preferably $C_{12}$ to $C_{24}$ fatty acids; paraffin waxes; water soluble starches (e.g., maltodextrin); and $C_8$ to $C_{20}$ alkanols (e.g., cetyl alcohol);

wherein the alkylene oxide compounds comprise at least 20%, preferably at least 40% of said structurant system and wherein the alkylene oxide compounds further comprise no more than about 70% by wt. of total composition;

It is a criticality of this invention to include the alkylene compounds in the bar composition, because the alkylene compounds serve as a dispersant and solvent for the alkoxylated nonionic surfactants of (c);

(c) Mildness Enhancement Agent and Co-structurant: 3% to 35% by wt. total composition of an alkoxylated nonionic surfactant;

wherein ratio of anionic surfactant to alkoxylated nonionic surfactant is between 1:1 to 10:1, preferably 2:1 to 7:1;

wherein ethylene oxide:hydrophobe mol ratio of said alkoxylated nonionic surfactant is between 7:1 and 40:1

(preferably between 15:1 and 25:1); This range of mol ratio is a criticality because, above this range, said alkoxylated nonionic surfactant is not as efficient at mitigating the skin irritation of anionics (see Example 1 and 2), and they are not as biodegradable. Below this range, the said alkoxylated nonionic surfactant can cause processing problems, such as stickiness during chill-rolling and plodding, and cause undesired user properties, such as mush and reduced lather;

wherein the melting temperature of the nonionic surfactant is between 25° C. and 85° C., preferably between 40° C. and 65° C.;

wherein the molecular weight of the said nonionic surfactants is between 500 and 3000 Dalton, preferably between 1000 and 2500 Dalton.

Surfactant System

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glycerol ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glycerol ether sulfates). among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

$$R^4O_2CCH_2CH(SO_3M)CO_2M; \text{ and}$$

amide-MEA sulfosuccinates of the formula:

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$R'CON(CH_3)CH_2CO_2M,$$

wherein R ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{18}$ alkyl, $R^3$ ranges from $C_1$–$C_4$ a alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of the total composition. Preferably, this component is present from about 30% to about 60%.

The acyl isethionate may be an alkoxylated isethionate such as is described in Ilardi et al., U.S. Pat. No. 5,393,466, hereby incorporated by reference. This compound has the general formula:

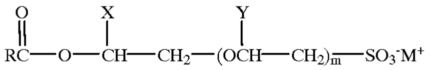

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

The anionic surfactant comprises 50% or more of the total surfactant system, but should comprise no more than 40% by wt. of the total composition.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula.

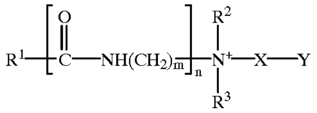

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

m is 2 to 4;

n is 0 to 1;

X is alkylene of 1 to 3 carbon atoms optionally substituted with hydroxyl, and

Y is $—CO_2—$ or $—SO_3—$

Suitable amphoteric detergents within the above general formula include simple betaines of formula:

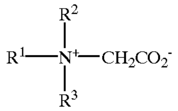

and amido betaines of formula:

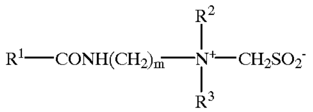

wherein m is 2 or 3.

In both formulae $R^1$, $R^2$, and $R^3$ are as defined previously. $R^1$ may in particular be a mixture of $C_{12}$ and $C_{14}$ alkyl groups derived from coconut so that at least half, preferably at least three quarters of the groups $R^1$ are preferably methyl. A further possibility is that the amphoteric detergent is a sulphobetaine of formula

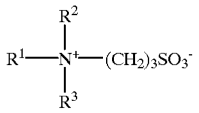

or

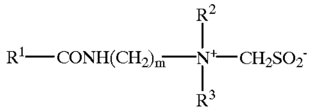

wherein m is 2 or 3, or variants of these in which $-(CH_2)_3SO_3^-$ is replaced by

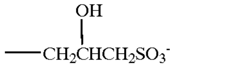

in these formulae $R^1$, $R^2$ and $R^3$ are as discussed previously.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamene Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. which is also incorporated into the subject application by reference.

Nonionic and cationic surfactants which may be used include any one of those described in U.S. Pat. No. 3,761,418 to Parran, Jr. hereby incorporated by reference into the subject application. Those included are the aldobionamides taught in U.S. Pat. No. 5,389,279 to Au et al. and the polyhydroxy fatty acid amides as taught in U.S. Pat. No. 5,312,934 to Letton, both of which are incorporated by reference into the subject application.

The surfactants generally comprise 10 to 70% of the total composition except, as noted that anionic comprises 50% or more of the surfactant system and no more than 40% total.

A preferred surfactant system is one comprising acyl isethionate and a amphoteric, i.e., betaine, as co-surfactant. Preferably, acyl isethionate comprises 10% to 70%, and more preferably 25 to 70% by wt. of the total composition, and amphoteric surfactant comprises 1% to 10% by wt. of the total composition.

Structurant

The structurant system of the invention is a mixture of water soluble alkylene oxide compounds and other structurants (i.e., fatty acid, maltodextrin and paraffin wax), wherein the alkylene oxide compounds comprise at least 20%, preferably at least 40% of said structurant system and wherein the alkylene oxide compounds further comprise no more than about 70% by wt. of total composition.

It is a criticality to include the alkylene oxide compounds in bar composition, because the alkylene oxide compounds serve as a dispersant and solvent for the alkoxylated nonionic surfactants of the subject invention.

Alkylene oxide compounds include moderately high molecular weight polyalkylene oxides of appropriate melting point (e.g.,25° to 100° C., preferably 45° C. to 65° C.) and in particular polyethylene glycols or mixtures thereof.

Polyethylene glycols (PEG's) which are used may have a molecular weight in the range 2,000 to 25,000, preferably 3,000 to 10,000. However, in some embodiments of this invention it is preferred to include a fairly small quantity of polyethylene glycol with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% or 1.5% to 4% or 4.5% by weight of the composition. These materials will generally be used jointly with a large quantity of other water soluble structurant such as the above mentioned polyethylene glycol of molecular weight 2,000 to 25,000, preferably 3,000 to 10,000.

Water soluble starches (e.g., maltodextrin) can also be included at levels of 1% to 15% by wt. of total composition.

Water insoluble structurants also have a melting point in the range 25–100° C., more preferably at least 45° C., notably 50° C. to 90° C. Suitable materials which are particularly envisaged are fatty acids, particularly those having a carbon chain of 12 to 24 carbon atoms. Examples are lauric, myristic, palmitic, stearic, arachidic and behenic acids and mixtures thereof. Sources of these fatty acids are coconut, topped coconut, palm, palm kernel, babassu and tallow fatty acids and partially or fully hardened fatty acids or distilled fatty acids. Other suitable water insoluble structurants include alkanols of 8 to 20 carbon atoms, particularly cetyl alcohol. These materials generally have a water solubility of less than 5 g/liter at 20° C.

Soaps, preferably with hydrocarbon chain longer than C14 (e.g., sodium stearate), can also be used at levels of about 1% to 15% by wt. of total composition. The soaps may be added neat or made in situ by adding a base, e.g., NaOH, to convert free fatty acids.

The relative proportions of the water soluble structurants and water insoluble structurants govern the rate at which the bar wears during use. The presence of the water-insoluble structurant tends to delay dissolution of the bar when exposed to water during use and hence retard the rate of wear.

The structurant is used in the bar in an amount of 20% to 85%, preferably 30% to 70% by wt., except, as noted, that alkylene oxide compounds should comprise no more than 70% wt. total composition.

Alkoxylated Nonionic Surfactants

The alkoxylated nonionic surfactants of the subject invention are generally commercially available polyoxyalkylene ethers of an alcohol of hydrophobic moiety, wherein the hydrophobic moiety can be derivatives of linear or branched alkyl, aryl, alkylaryl, alkylene, acyl; fat and oil derivatives of alkylglyceryl, glyceryl, sorbitol, lanolin oil, coconut oil, jojoba oil, castor oil, almond oil, peanut oil, wheat germ oil, rice bran oil, linseed oil, apricot pits oil, walnuts, palm nuts, pistachio nuts, sesame seeds, rapeseed, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, etc.;

The mol ratio of ethylene oxide:hydrophobic moiety of said alkoxylated nonionic surfactant is in the range of 7:1 to 40:1, preferably 15:1 to 25:1. This range of mol ratio is a criticality, because above this range, alkoxylated nonionic surfactants are not as efficient at mitigating the skin irritation of anionics (see Example 1 and Example 2), and they are not as biodegradable (based on the public literature from Albright & Wilson). Below this range, the nonionic surfactants can cause processing problems, such as stickiness during chill rolling and plodding, and cause undesired user properties, such as mush and reduced lather.

In general, the molecular weight of alkoxylated nonionic surfactant is between 500 and 3000 Dalton, preferably 1000 and 2500 Dalton. The specifications on the molecular weight provide the alkoxylated surfactants with a preferred range of melting temperature from 20° to 85°, most preferably 40° to 65° C., the latter being more favorable for processing and desired user properties (e.g., chips form more easily, logs plod more readily, and bars with adequate firmness and smoothness).

The weight ratio of anionic surfactant to alkoxylated nonionic surfactant is between 1:1 to 10:1, preferably 2:1 to 7:1. This range of weight ratio is a criticality because, above this range, the skin irritation of the anionics can not be effectively mitigated; below the range, bar processability and user properties, such as lather performance, can be negatively affected.

Specifically, examples of various alkoxylated nonionic surfactants are set forth in Table 1 below wherein $T_m$ (° C) were obtained from literature from suppliers or measured by the inventors using a differential scanning calorimetry (DSC) device.

TABLE 1

Representative Alkoxylated Nonionic Surfactants

| Chemicals | Supplies (Brands) | Comments |
|---|---|---|
| POE(20) cetyl ether | Nikko Chemicals (BC-20) | white solid, Tm = 46.3 C. |
| POE(20) oleyl ether | ICI (BRIJ 98) | white tacky solid; Tm > 20 C. |
| POE(20) sorbitan isostearate | SEPPIC (Montanox) Tm > 25 C. | white tacky solid, |
| POE(25) cetyl ether | Nikko Chemicals (BC-40) | white solid, Tm = 48.7 C. |
| POE(32) distearate | Armak (Kessco PEG 1540 distearate) | white tacky solid; Tm > 20 C. |

Bars of the invention may comprise 0% to 25%, preferably 2% to 15% by wt. of an emollient such as ethylene glycol, propylene glycol and/or glycerine.

Other Ingredients

Bar compositions of this invention will usually contain water, but the amount of water is only a fairly small proportion of the bar. Larger quantities of water reduce the hardness of the bars. Preferred is that the quantity of water is not over 15% by weight of the bars, preferably 1% to about 10%, more preferably 3% to 9%, most preferably 3% to 8%.

Bars of this invention may optionally include so-called benefit agents—materials included in relatively small proportions which confer some benefit additional to the basic cleansing action of the bars. Examples of such agents are: skin conditioning agents, including emollients such as fatty alcohols and vegetable oils, essential oils, waxes, phospholipids, lanolin, anti-bacterial agents and sanitizers, opacifiers, pearlescers, electrolytes, perfumes, sunscreens, fluorescers and coloring agents. Preferred skin conditioning agents comprise silicone oils, mineral oils and/or glycerol.

The examples below are intended to better illustrate the invention, but are not intended to be limiting in any way.

All percentages, unless otherwise noted, are intended to be percentages by weight.

EXAMPLES

Methodology

Mildness Assessments

Zein dissolution test was used to preliminarily screen the irritation potential of the formulations studied. In an 8 oz. jar, 30 mLs of an aqueous dispersion of a formulation were prepared. The dispersions sat in a 45° C. bath until fully dissolved. Upon equilibration at room temperature, 1.5 gms of zein powder were added to each solution with rapid stirring for one hour. The solutions were then transferred to centrifuge tubes and centrifuged for 30 minutes at approximately 3,000 rpms. The undissolved zein was isolated, rinsed and allowed to dry in a 60° C. vacuum oven to a constant weight. The percent zein solubilized, which is proportional to irritation potential, was determined gravimetrically.

The Protocol of 3-Day Patch Test

Patch test was used to evaluate skin mildness of aqueous dispersions containing 1% DEFI active (sodium cocoyl isethionate) and different levels of the structurant/coactives. Patches (Hilltop(R) Chambers, 25 mm in size) were applied to the outer upper arms of the panelists under bandage type dressings (Scanpor(R) tape). After each designated contact periods (24 hrs. for the first patch application, 18 hrs. for the second and third applications), the patches were removed and the sites were visually ranked in order of severity (erythema and dryness) by trained examiners under consistent lighting. Ps Formulation Processing Bar formulations were prepared in a 2-liter Patterson mixer with a sigma type blade. The components were mixed together at ~95° C., and the water level was adjusted to approximately 8–10 wt. %. The batch was covered to prevent moisture loss, and mixed for about 15 minutes. Then the cover was removed and the mixture was allowed to dry. The moisture content of the samples taken at different times during the drying stage was determined by Karl Fisher titration with a turbo titrator. At the final moisture level (~5%), the formulation was dropped onto a heated applicator roll and then was chipped over a chill roll. The chill roll chips were plodded under vacuum in a Weber Seelander duplex refiner with screw speed at ~20 rpm. The nose cone of the plodder was heated to 45–50° C. The cut billets were stamped into bars using a Weber Seelander L4 hydraulic press with a nylon, pillow-shaped die in place.

Bars were also prepared by a cast-melt process. First, the components were mixed together at 80–120° C. in a 500 ml beaker, and the water level was adjusted to approximately 10–15 wt. %. The batch was covered to prevent moisture loss and was mixed for about 15 minutes. Then the cover was removed, and the mixture was allowed to dry. The moisture content of the samples taken at different times during the drying stage and was determined by Karl Fisher titration with a turbo titrator. At the final moisture level (~5%), the mixture in the beaker (in the form of a free-flow liquid) was dropped into bar-molds and was allowed to be cooled at room temperature for four hours. Upon solidification, the mixture was casted in the bar mold into a bar.

Example 1

Components as listed in Table 2 below were melted together at 80° C.–120° C. to produce a material consisting predominantly of a liquid phase. All amounts are provided in percentage by weight. On cooling to 10° C.–50° C. by a chill-roll, the formulations formed plastic-like solids that were plodded using the extrusion equipment described above (i.e., formulation processing section) and pressed into bars using the single bar press. Identical formulations were also formed into bars by using the casting process from the hot melt. These bars contain a major DEFI active and an optional cocoamidopropyl betaine coactive. These bars provided rich, creamy and slippery lather; the skin-feel of the bars were found to be smooth and non-tacky.

TABLE 2

| Formulation | A | B | C | D |
|---|---|---|---|---|
| Sodium acyl isethionate (from DEFI*) | 27.8% | 27.0% | 27.0% | 27.8% |
| Cocoamidopropyl betaine | 5.2 | 5.0 | 5.0 | 5.2 |
| PEG 8000** | 32.1 | 29.5 | 35.0 | 45.1 |
| PEG 4000*** | 3.1 | 0.0 | 0.0 | 0 |
| Stearic-palmitic acid | 11.6 | 8.6 | 9.0 | 11.6 |
| Maltodextrin | 10.3 | 10.0 | 0.0 | 4.4 |
| POE(23) cetyl ether | 4.0 | 5 | 10 | 0.0 |
| POE(20) cetyl ether | 0 | 5 | 0 | 0 |
| Perfume | 0 | 0.3 | 0.3 | 0 |
| Sodium Stearate | 0 | 0 | 5.0 | 0 |
| Titanium Dioxide | 0 | 0 | 0.5 | 0 |
| EHDP | 0 | 0.1 | 0.1 | 0 |
| EDTA | 0 | 0.1 | 0.1 | 0 |
| Misc. Salts | 0 | 2.9 | 2.9 | 0 |
| Water | 5.9 | 6.5 | 5.1 | 5.9 |

*DEFI: directly esterified fatty acid isethionate, which is a mixture containing about 74% by weight of fatty acyl isethionate, 23% stearic-palmitic acid and small amounts of other materials, manufactured by Lever Brothers Co., U.S.
**PEG 8000: polyoxyethylene glycol with mean molecular weigh at 8000;
PEG 4000: polyoxyethylene glycol with mean molecular weight at 4000.

Example 2

Components as listed in Table 3 below were preferably processed using a cast-melt approach described in the methodology section. All amounts are given in percentage of weight. These bars used sodium lauryl sarcosinate (formulation E, G) and sodium lauryl sulphate (formulation F) as the major anionic detergent with optional cocoamidopropyl betaine as a coactive. These bars provided rich, creamy and slippery lather and smooth skin feel.

TABLE 3

| Formulation | (E) | (F) | (G) |
|---|---|---|---|
| Sodium Lauryl Sarcosinate | 15 | 0.0 | 27.0 |
| Cocoamidopropyl Betaine | 5.0 | 5.0 | 5.0 |
| SLES (3EO) | 5.0 | 20.0 | 0.0 |
| Stearic-palmitic Acid | 5.0 | 5.0 | 5.0 |
| PEG 8000 | 25.0 | 44.0 | 39.0 |
| PEG 6000 | 27.0 | 8.0 | 5.0 |
| POE(40) cetyl ether | 10.0 | 10.0 | 10.0 |
| Paraffin Wax | 2.0 | 2.0 | 3.0 |
| Perfumes | 1.0 | 1.0 | 1.0 |
| Water | 5.0 | 5.0 | 5.0 |

Example 3

The irritation reduction potential of alkoxylated nonionic surfactants was investigated using Zein dissolution experiments. As indicated in FIG. 1, alkoxylated nonionic surfactants, as a class, are significantly more effective than PEG 8000 in reducing the Zein % wt. dissolved by an aqueous DEFI/Cocoamido propyl betaine surfactant system (DEFI is a sodium acyl isethionate/fatty acid mixture defined in the Table 2 of Example 1).

The data in FIG. 1 also showed that the nonionic surfactants with ethylene oxide:hydrophobe mol ratio below 30:1 are potentially better mildness enhancers than the ones with higher mol ratios. Additionally, the nonionics with the mol ratio below 30:1 are more biodegradable than the ones with higher ratios (based on the public literature from Albright & Wilson).

Example 4

Figure 2:
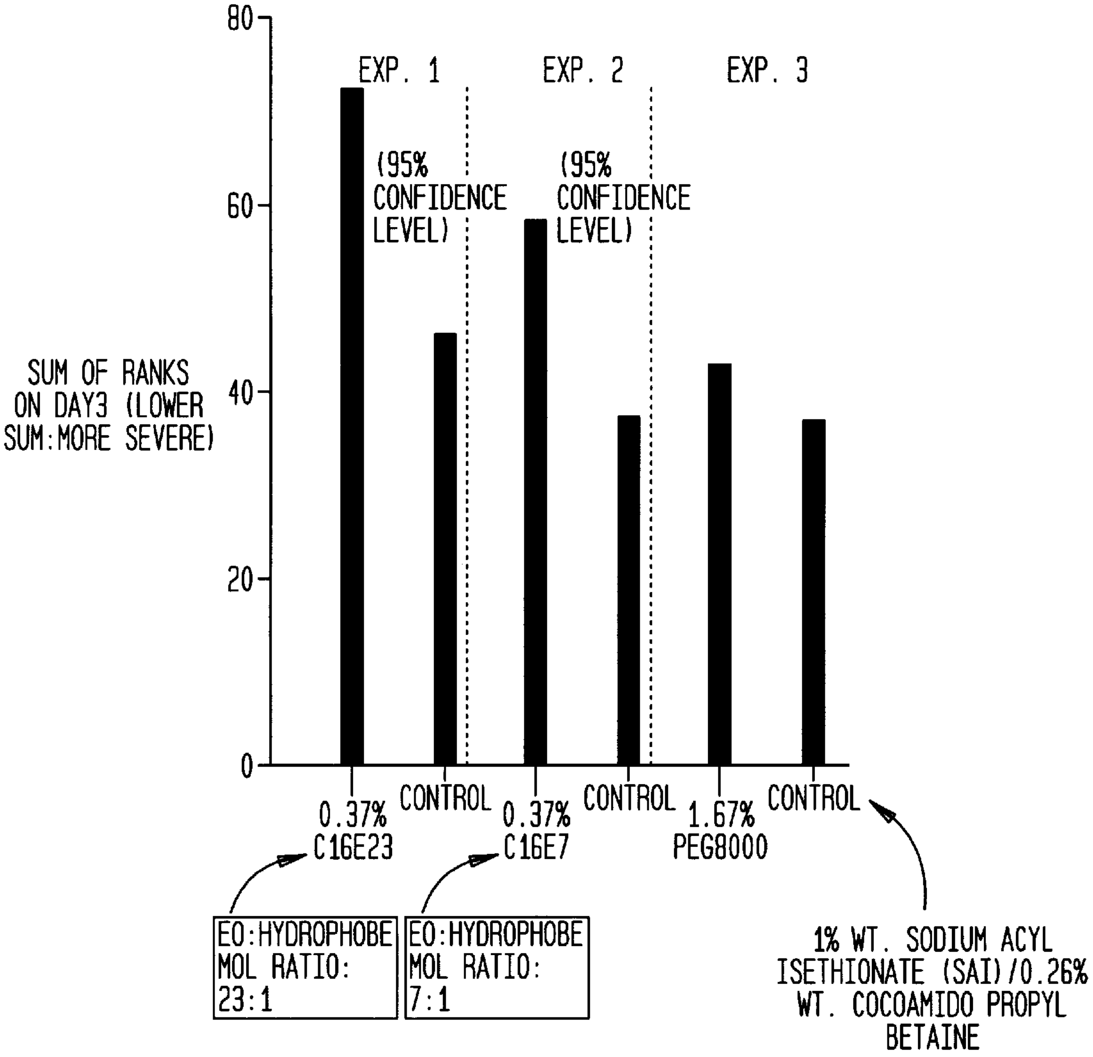
FIG. 2 shows the alkoxylated nonionic surfactants of the invention (especially those with lower ethylene oxide:hydrophobe mol ratio) significantly reduces skin irritation caused by DEFI, a mixture of sodium acyl isethionate and fatty acid (defined in Table 2, Example 1).

Three day skin patch tests showed that the alkoxylated nonionic surfactants with lower ethylene oxide:hydrophobe mol ratios (<30:1) significantly reduced the skin irritation caused by DEFI, even at low levels of addition. As shown in FIG. 2, at a sodium acyl isethionate (SAI): nonionic weight ratio around 1:0.37 (equivalent to 10% alkoxylated nonionic surfactant in the bar of Formulation (B) or (C) in Table 2 of Example 1), the nonionic surfactants reduced the skin irritation of a DEFI/betaine liquor significantly. In contrast, even at SAI/PEG 8000 weight ratio as low as 1:1.67 (effectively 45% PEG 8000 in the bar of formulation D, Table 2) PEG 8000 made no measurable mildness contribution to the SAI/CAP betaine aqueous liquor.

We claim:

1. A bar composition comprising:

(a) 10% to 70% by wt. total composition of a surfactant system selected from the group consisting of anionic surfactants, nonionic surfactants (other than the specific polyoxyalkylene ethers of an alcohol of a hydrophobic group defined in (c)), cationic surfactants, amphoteric surfactants and mixtures thereof;

wherein the anionic surfactant comprises at least 50% of said surfactant system and wherein the anionic component further comprises no more than about 40% by wt. of total composition;

(b) 20% to 85% by wt. total composition of a bar structurant selected from the group consisting of alkylene oxide compounds having a molecular weight of from about 2000 to about 25,000; $C_8$–$C_{22}$ free fatty acids, paraffin waxes; water soluble starches, and $C_8$–$C_{20}$ alkanols;

wherein the alkylene oxide compounds comprise at least 20% of said structurant system and wherein the alkylene oxide compounds further comprise no more than about 70% by wt. of total composition;

(c) 3% to 35% by wt. total composition of a surfactant which is a polyoxyalkylene ether of an alcohol of a hydrophobic group and wherein said hydrophobic group is an alkyl group;

wherein weight ratio of anionic surfactant (a) to surfactant (c) is between 1:1 to 10:1; wherein alkylene oxide:hydrophobic moiety mol ratio of said surfactant (c) is between 15:1 and 30:1; wherein the melting temperature of the surfactant (c) is between 25° C. and 85° C.; and wherein the molecular weight of said surfactant (c) is between 500 and 3000 Dalton.

2. A composition according to claim 1 wherein surfactant system comprises anionic, amphoteric or mixtures thereof.

3. A composition according to claim 1, wherein surfactant comprises acyl isethionate and betaine.

4. A composition according to claim 1, wherein structurant (b) comprises 30% to 70% of the bar.

5. A composition according to claim 1, wherein the said structurant system (b) contains fatty acid soap in the level of 1% to 15% by weight of total composition.

6. A composition according to claim 1, wherein molecular wt. of the alkylene oxide compounds in (b) is 3,000 to 10,000.

7. A composition according to claim 1, wherein the said structurant system (b) contains at least 40% wt. of said alkylene oxide compounds.

8. A composition according to claim 1, wherein melting temperature of (c) is 40° C. to 65° C.

9. A composition according to claim 1, wherein alkylene oxide:hydrophobic moiety mol ratio of (c) is between 15:1 and 25:1.

10. A composition according to claim 1, wherein the anionic surfactant (a) to surfactant (c) weight ratio is between 2:1 and 7:1.

11. A composition according to claim 1, wherein the molecular weight of (c) is between 1000 and 2500 Dalton.

12. A composition according to claim 1, additionally comprising a polyol.

13. A composition according to claim 12, wherein said polyol is selected from the group consisting of ethylene glycol, propylene glycol, glycerol and mixtures thereof.

14. A composition according to claim 1, wherein the water soluble starch of (b) is maltodextrin.

* * * * *